US008978168B2

(12) United States Patent
Chiang

(10) Patent No.: US 8,978,168 B2
(45) Date of Patent: Mar. 17, 2015

(54) SWIM GOGGLES

(75) Inventor: Herman Chiang, Taipei Hsien (TW)

(73) Assignee: Global Esprit Inc., Chung-Ho, Taipei Hsien (TW)

( * ) Notice: Subject to any disclaimer, the term of this patent is extended or adjusted under 35 U.S.C. 154(b) by 1187 days.

(21) Appl. No.: 12/789,994

(22) Filed: May 28, 2010

(65) Prior Publication Data

US 2011/0271432 A1 Nov. 10, 2011

(30) Foreign Application Priority Data

May 6, 2010 (TW) ................................ 99208420 U

(51) Int. Cl.
*A63B 33/00* (2006.01)
*G02C 11/08* (2006.01)
*A61F 9/02* (2006.01)

(52) U.S. Cl.
CPC .............. *A63B 33/002* (2013.01); *G02C 11/08* (2013.01); *A61F 9/025* (2013.01)
USPC ................ 2/438; 2/426; 2/428; 2/429; 2/434; 2/440; 351/43

(58) Field of Classification Search
CPC .................................. A61F 9/02; A61F 9/025
USPC ............. 2/438, 440, 426, 429, 441, 443, 448, 2/428, 434; 351/43; 12/438, 440
See application file for complete search history.

(56) References Cited

U.S. PATENT DOCUMENTS

| 4,689,838 | A | * | 9/1987 | Angermann et al. | ............. 2/441 |
| 5,363,512 | A | * | 11/1994 | Grabos et al. | ..................... 2/436 |
| 5,542,130 | A | * | 8/1996 | Grabos et al. | ..................... 2/436 |
| 5,628,072 | A | * | 5/1997 | Haslbeck et al. | ................. 2/428 |
| 5,857,221 | A | * | 1/1999 | Geneve et al. | ..................... 2/428 |
| 7,604,346 | B2 | * | 10/2009 | Wang | .............................. 351/43 |
| 2001/0034896 | A1 | | 11/2001 | Chiang | |
| 2002/0170108 | A1 | | 11/2002 | Chiang | |

FOREIGN PATENT DOCUMENTS

| EP | 0525238 A1 | 2/1993 |
| EP | 1008369 A1 | 6/2000 |
| EP | 1382370 A1 | 1/2004 |
| GB | 2428812 A | 2/2007 |

* cited by examiner

*Primary Examiner* — Danny Worrell
*Assistant Examiner* — Khaled Annis
(74) *Attorney, Agent, or Firm* — Cheng-Ju Chiang

(57) ABSTRACT

A pair of swim goggles include a connecting frame being assembled with a left lens frame and a right lens frame and a head strap, characterized in that the left and the right lens frames respectively have a lens and a frame body, an upper side and a lower side of the frame body respectively provided with a track thereon, the connecting frame including a first rib and a second rib spaced apart from each other and respectively defining a connection part thereon for being detachably coupled with the respective track, whereby the left and the right lens frames are detachably and separately assembled with the respective first rib and second rib and therefore are slidable with respect to the first and the second ribs though the track.

9 Claims, 5 Drawing Sheets

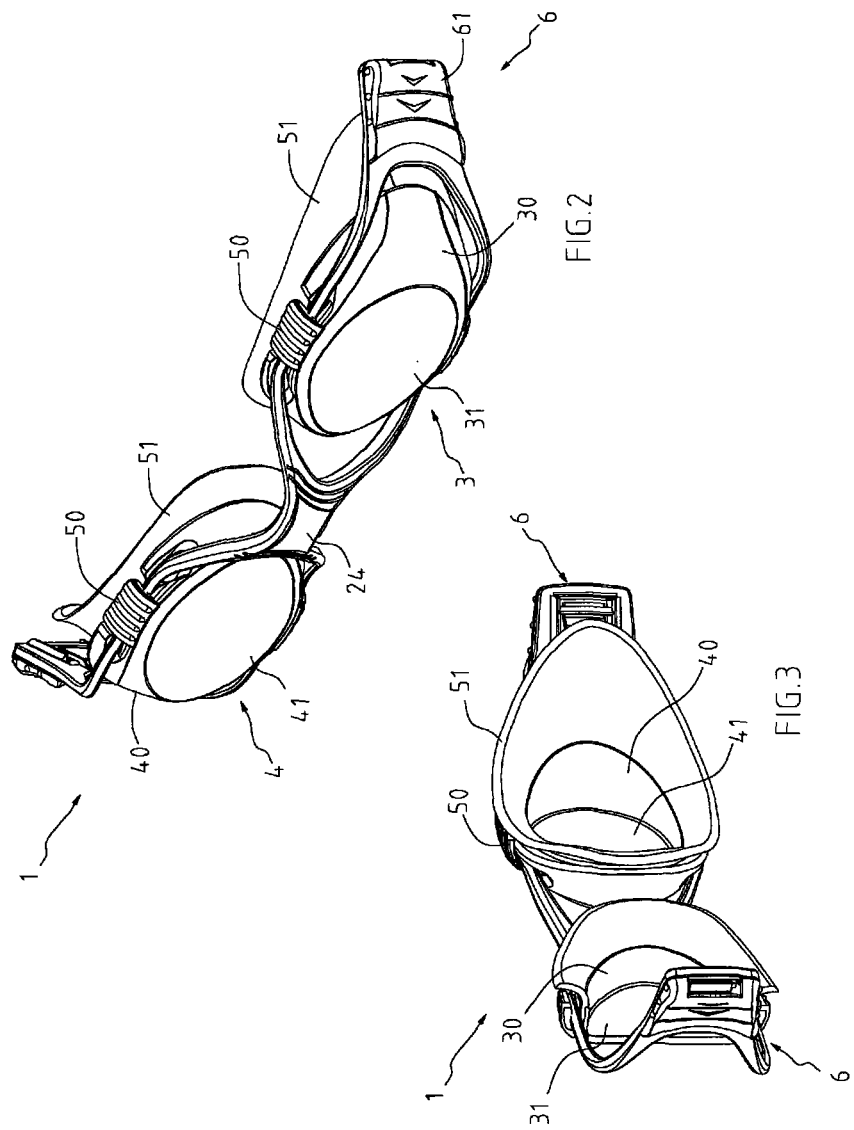

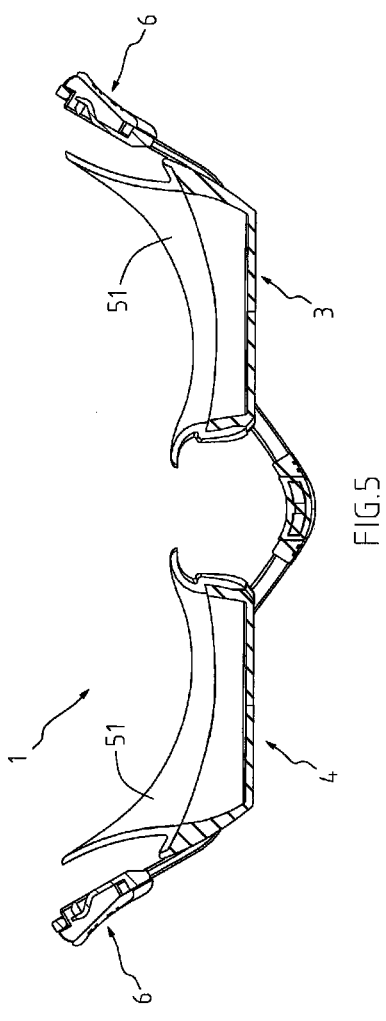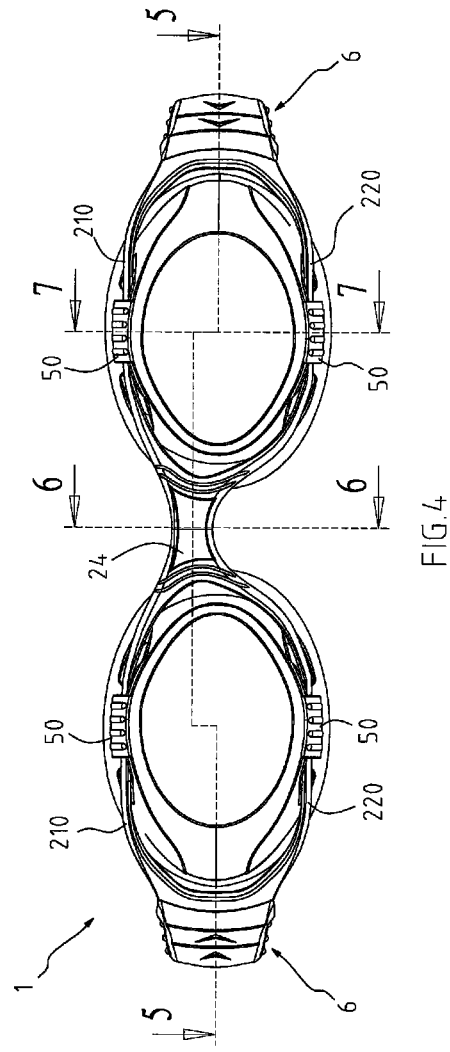

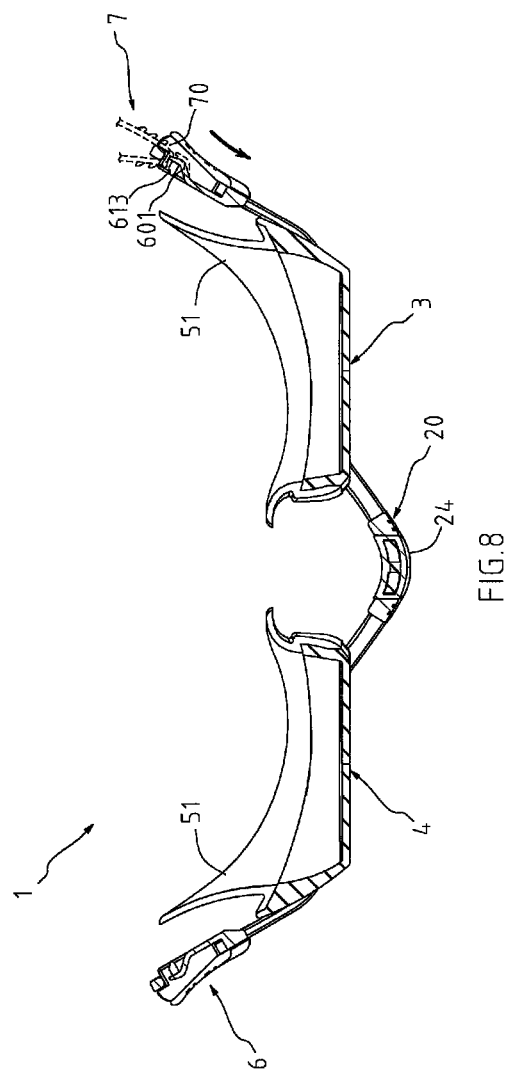

SWIM GOGGLES

BACKGROUND OF THE INVENTION

1. Field of the Invention

The present invention relates to a pair of swim goggles, and particularly to a pair of swim goggles for the use in a swimming pool, wherein a left lens frame and a right lens frame of the swim goggles are detachably and separately assembled with a connecting frame and adjustable in transverse with respect to the connecting frame.

2. Related Art

Conventional swim goggles for the use in a swimming pool are generally of a left and a right lens frames, which are varied in structure by functions or purposes of such as comfort of wearing, adjustment of head strap, or leak-proof and so on, wherein the left and right lens frames are generally connected by a connecting element, which is able to be used for adjusting a span between the left and right lens frames, however, such adjustment acted by the connecting element is easily to affect positions of both the left and right lens frames and therefore either the left lens frame or right lens frame cannot be well fitted to the eye sockets.

Accordingly, another type of swim goggles is improved by using two head straps respectively set along upper and lower sides of the left and right lens frames so as to adjust positions of the left and right lens frames individually and respectively. As a result, while adjusting one of the lens frames, the other one will not be affected. However, aforementioned conventional swim goggles are still used inconveniently or incapability when one of the lenses is needed to be replaced, such us the lens is broken or scratched or of different shortsighted degrees. Hence it is imperative to develop novel swim goggles of which lenses can be replaced separately, quickly and effectively and thereby overcome the foregoing drawbacks.

SUMMARY OF THE INVENTION

Accordingly, an object of the present invention is to provide novel swim goggles of which a left lens frame and a right lens frame are detachably and separately assembled and adjustable.

To achieve the above-mentioned objects, a pair of swim goggles includes a connecting frame being assembled with a left lens frame and a right lens frame and a head strap, characterized in that the left and the right lens frames respectively having a lens and a frame body formed integrally with and around a periphery of the lens, an upper side and a lower side of the frame body respectively provided with a track thereon, the connecting frame including a middle portion, a first rib and a second rib being spaced apart from each other, and a pair of joint members for allowing the head strap being drawn therethrough, the first and the second ribs respectively defining a connection part thereon for being detachably coupled with the respective track, whereby the left and the right lens frames are detachably and separately assembled with the respective first rib and second rib and therefore are slidable with respect to the first and the second ribs though the track.

BRIEF DESCRIPTION OF THE DRAWINGS

FIG. 2 is a perspective assembly view of FIG. 1;

FIG. 3 is a schematic view of FIG. 2 viewed from a different angle;

FIG. 4 is a front elevation view of FIG. 2;

FIG. 5 is a cross-sectional view taken along a line 5-5 in FIG. 4;

FIG. 8 is a schematic view showing how a head strap is released.

DESCRIPTION OF THE PREFERRED EMBODIMENTS

Figure 1:
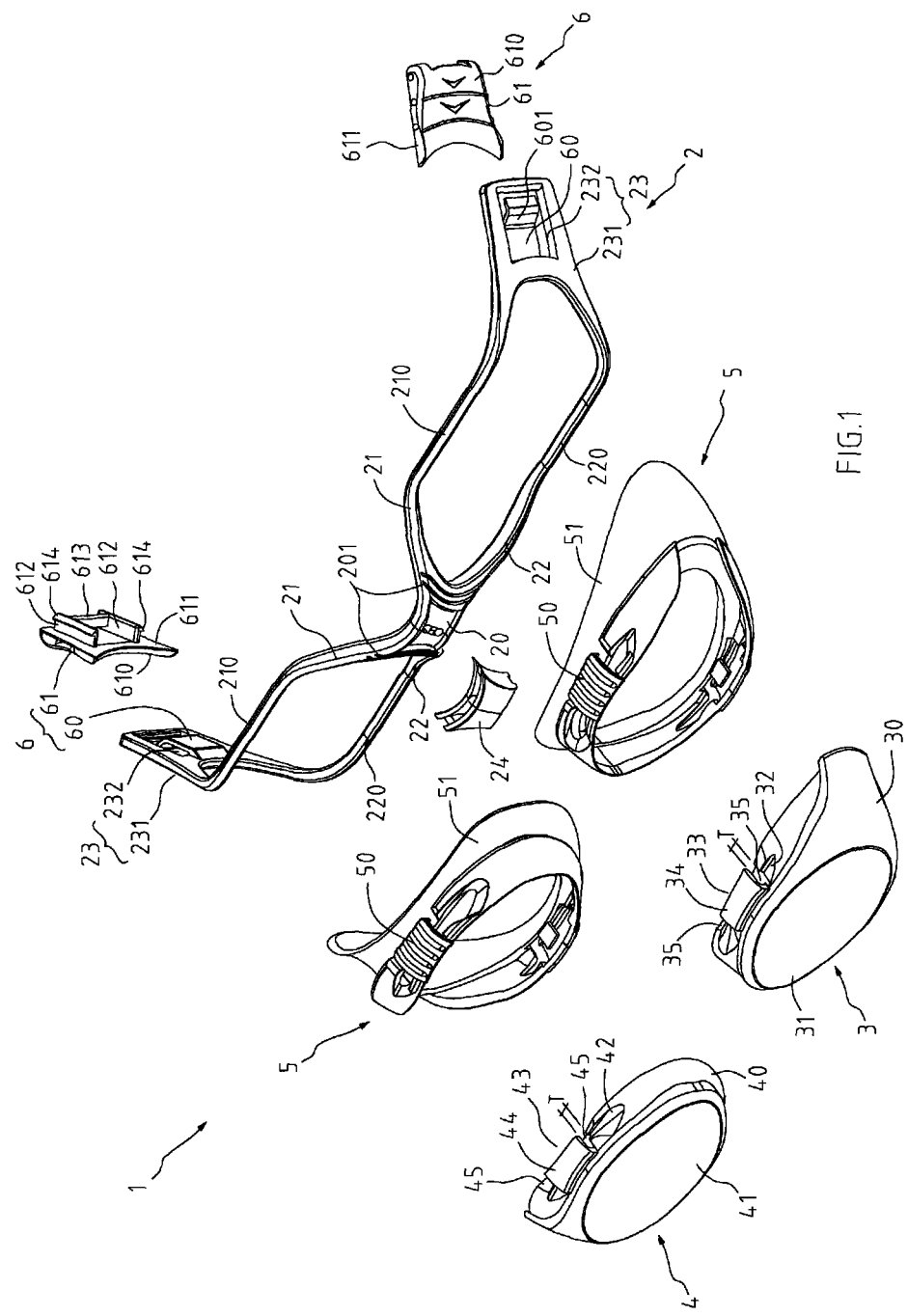
FIG. 1 is a perspective exploded view of a pair of swim goggles of the present invention.
Figure 7:
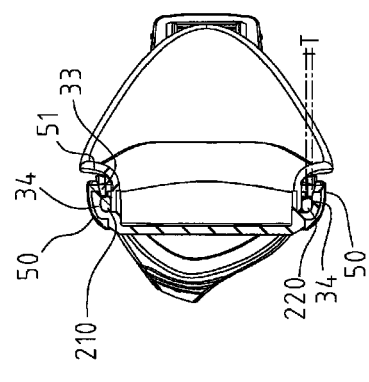
FIG. 7 is a cross-sectional view taken along a line 7-7 in FIG. 4.
Figure 6:
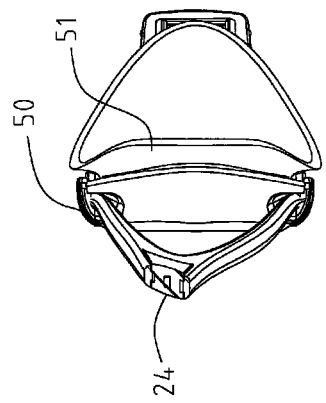
FIG. 6 is a cross-sectional view taken along a line 6-6 in FIG. 4.

Referring to FIGS. 1 and 7, the swim goggles 1 comprise a connecting frame 2 being assembled with a left lens frame 3, a right lens frame 4, a covering frame 5, and a buckling apparatus 6 and a head strap 7 of a plurality of retaining slots 70 (referring to FIG. 8), wherein the connecting frame 2 made of NYLON includes a middle portion 20, a first rib 21 and a second rib 22 both extending longitudinally outwardly from opposite sides of the middle portion 20 and being spaced apart from each other, and a pair of joint members 23 for joining the first rib 21 and the second ribs 22 at one end thereof opposite to the middle portion 20, respectively, and for allowing the head strap 7 being drawn through, wherein the middle portion 20 protrudes outwardly from the first and the second ribs, 21, 22 and has a plurality of grooves 201 at the opposite sides thereof for providing better flexibility in order to fit various sizes of wearers' nose bridges. In addition, the middle portion 20 has a soft pad 24 which is made of Thermal Plastic Rubber (TPR) and formed integrally with the middle portion 20 (referring to FIG. 6). The first rib 21 and the second rib 22 respectively define a connection part 210, 220 thereon which are in substantially parallel with each other (coplanar) and are straight and able to be detachably coupled with respective track 32, 42 (described below). Each of the joint members 23 has a base 231 and an opening 232 defined in the base 231, wherein the opening 232 is provided for the head strap 7 drawn therethrough.

The left lens frame 3 and the right lens frame 4 are of the same structure and preferably made of Polycarbonate (PC), respectively having a lens 31, 41 and a frame body 30, 40 formed integrally with and around a periphery of the lens 31, 41, an upper side and a lower side of the frame body 30, 40 is respectively provided with the track 32, 42 thereon, and the track 32, 42 is substantially centrally provided with a notch 33, 43 protruding inwardly of the frame body 30, 40, and a holding plate 34, 44 protrudes from one side of the track 32, 42 respective to the notch 33, 43 so as to form a gap T between the notch 33, 43 and the holding plate 34, 44 (referring to FIGS. 1 and 7); in addition, a width of the holding plate 34, 44 is less than a width of the notch 33, 43 so as to form a clipping slit 35, 45 between the track 32, 42 and the holding plate 34, 44 in cross-section, the clipping slit 35, 45 communicating with the notch 33, 43 and the gap T; through the gap T and the clipping slit 35, 45, the connection part 210 of the first rib 21 and the connection part 220 of the second rib 22 are detachably coupled with the respective track 32, 42, namely, the gap T facilitates assembly of the connection part 210, 220 of the first and the second ribs 21, 22 and the track 32, 42, and the connection part 210, 220 is effectively positioned in the track 32, 42 by the clipping slit 35, 45.

The covering frame 5 with a hollow portion (not labeled) corresponding to the track 32, 42 is preferably made of TPR and sealingly covers the upper and bottom sides of the frame body 30, 40 and the holding plate 34, 44. A plurality of ridges 50 are formed on the covering frame 5 with respect to the holding plate 34, 44 for increasing a frictional area in the interest of the wearers' manipulation. Furthermore, a contact skirt 51 integrally extends rearward from the covering frame 5 for being fitted to an area around wearers' eye sockets.

The buckling apparatus 6 is adjustably coupled with the joint member 23 of the connecting frame 2 for selectively engaging the head strap 7, the buckling apparatus 6 having a flexible engaged board 60 and a released board 61, one end of the flexible engaged board 60 integrally formed with the joint member 23, another end of the flexible engaged board 60 extending obliquely to form a guiding wall 601 in the opening 232, the released board 61 having an outside surface 610 and an inside surface 611 opposite to the outside surface 610, wherein the outside surface 610 is being rough and has a symbol of released direction (not labeled); two opposite sides of the inside surface 611 are provided with a leading wall 612, respectively, corresponding to two opposite sides of the opening 232, a biasing wall 613 is disposed between the leading walls 612 with respect to the guiding wall 601 and is spaced away from the inside surface 611, and each of the leading walls 612 has a flange 614 on one edge thereof. In assembly, the leading walls 612 of the released board 61 are installed into the opening 232 with the flanges 614 being against the respect side of the opening 232 where the guiding wall 601 is disposed between the biasing wall 613 and the inside surface 611 of the released board 61.

Referring to FIG. 8, after assembly of the swim goggles 1, one of the retaining slots 70 of the head strap 7 is selectively engaged against the guiding wall 601 of the flexible engaged board 60 so that the head strap 7 is allowed to move only in one-way direction, and once the head strap 7 is intended to be released, the released board 61 is being pushed in a reverse direction with respect to the one-way direction as pointed by an arrow shown in FIG. 8, simultaneously, the biasing wall 613 moves against the guiding wall 601 (as shown as broken lines) so that the guiding wall 601 is disengaged from the one of the retaining slots 70 and the head strap 7 is therefore able to be drawn freely from any direction. Once the released board 61 is not being pushed, the guiding wall 601 will bounce back to its previous position to be against one of the retaining slots 70 due to flexibility of the flexible engaged board 60.

Accordingly, the left lens frame 3 and the right lens frame 4 of the swim goggles 1 can be replaced separately, quickly and effectively when the lenses 31, 41 are broken or scratched or required for different shortsighted degrees. Furthermore, the left and the right lens frames 3, 4 can be adjusted easily by moving along the first and the second ribs 21, 22.

It is understood that the invention may be embodied in other forms within the scope of the claims. Thus the present examples and embodiments are to be considered in all respects as illustrative, and not restrictive, of the invention defined by the claims.

What is claimed is:

1. A pair of swim goggles, comprising a connecting frame being separately assembled with a left lens frame and a right lens frame and a head strap, wherein the left and the right lens frames respectively comprise a lens and a frame body formed integrally with and around a periphery of the lens, an upper side and a lower side of the frame body being respectively provided with a track thereon; and the connecting frame including a middle portion, a first rib and a second rib respectively extending longitudinally outwardly from opposite sides of the middle portion and being spaced apart from each other, and a pair of joint members for joining the first and the second ribs at one end thereof opposite to the middle portion, respectively, and for the head strap being drawn therethrough, each of the first and the second ribs defining a connection part thereon for being detachably coupled with the track;

wherein the track is substantially centrally provided with a notch protruding inwardly of the frame body, and a holding plate protrudes from one side of the track with respect to the notch so as to form a gap between the notch and the holding plate, wherein a width of the holding plate is less than a width of the notch so as to form a clipping slit between the track and the holding plate in cross-section, the clipping slit communicating with the notch and the gap; and wherein the connection part of the first rib and the connection part of the second rib are designed to be coplanar with each other wherein the first rib and the second rib are detachably disposed on the respective track through the gap; the swim goggles further comprises a covering frame made of thermal plastic rubber (TPR) for covering at least the upper side and the lower side of the frame body and the holding plate of the left and the right lens frames; a contact skirt integrally extends rearward from the covering frame and adapted to fit a wearer's eye socket;

wherein the left lens frame and the right lens frame are detachably and separately assembled with the connection part defined by each of the first rib and the second rib and therefore the left and the right lens frames are slidable with respect to the first and the second ribs through the track.

2. The swim goggles of claim 1, wherein a plurality of ridges are formed on the covering frame with respect to the holding plate for increasing a frictional area in the interest of a wearer's manipulation.

3. The swim goggles of claim 1, wherein the left lens frame and the right lens frame are made of polycarbonate (PC).

4. The swim goggles of claim 1, wherein the connecting frame is made of nylon, the middle portion having a plurality of grooves at the opposite sides thereof for providing better flexibility.

5. The swim goggles of claim 4, wherein the middle portion of the connecting frame further has a soft pad made of thermal plastic rubber (TPR), the soft pad being formed integrally with the middle portion.

6. The swim goggles of claim 1, wherein the joint member of the connecting frame includes a base and an opening defined in the base, the opening being provided for the head strap drawn therethrough.

7. The swim goggles of claim 1, wherein two opposite ends of the head strap have a plurality of retaining slots.

8. The swim goggles of claim 7, further comprising a buckling apparatus adjustably coupled with the joint member of the connecting frame for selectively engaging the head strap, the buckling apparatus having a flexible engaged board and a released board, one end of the flexible engaged board integrally formed with the joint member, another end of the flexible engaged board extending obliquely to form a guiding wall in an opening, the released board having an outside surface and inside surface opposite to the outside surface, two opposite sides of the inside surface being provided with a leading wall, respectively, corresponding to two opposite sides of the opening, a biasing wall being disposed between the leading walls with respect to the guiding wall, each of the leading walls having a flange on one edge thereof, whereby one of the retaining slots of the head strap is selectively engaged against the guiding wall of the flexible engaged board so that the head strap is allowed to move only in one-way direction, and while the released board is pushed in a reverse direction with respect to the one-way direction, the biasing wall moves against the guiding wall so that the guiding wall is disengaged from one of the retaining slots and the head strap is therefore able to be drawn freely.

9. The swim goggles of claim 8, wherein the outside surface of the released board has a symbol of released direction.

\* \* \* \* \*